United States Patent [19]
Rothgery et al.

[11] 4,139,622
[45] Feb. 13, 1979

[54] METHOD OF CONTROLLING FUNGI USING PHTHALAZINE COMPOUNDS

[75] Inventors: Eugene F. Rothgery, North Branford; Hansjuergen A. Schroeder, Hamden, both of Conn.

[73] Assignee: Olin Corporation, New Haven, Conn.

[21] Appl. No.: 844,004

[22] Filed: Oct. 20, 1977

[51] Int. Cl.$^2$ ................ C07D 237/30; A61K 31/495
[52] U.S. Cl. ..................................... 424/250; 544/237
[58] Field of Search ........................ 424/250; 544/237

[56] References Cited

U.S. PATENT DOCUMENTS

| 2,835,626 | 5/1958 | Margot et al. | 260/250 P |
| 3,260,588 | 7/1966 | Schroeder | 260/250 P |
| 3,260,725 | 7/1966 | Schroeder | 260/250 P |

Primary Examiner—Nicholas S. Rizzo
Attorney, Agent, or Firm—William A. Simons; Thomas P. O'Day

[57] ABSTRACT 1-halo- and 1-lower alkoxy-4-trichloromethylphthalazines are disclosed as fungicides and as novel compositions of matter.

5 Claims, No Drawings

METHOD OF CONTROLLING FUNGI USING PHTHALAZINE COMPOUNDS

BACKGROUND OF THE INVENTION

1. Field of the Present Invention

The present invention relates to 1-halo- or 1-lower alkoxy-4-trichloromethylphthalazines and their use as fungicides.

2. Description of the Prior Art

Heterocyclic ring compounds which have both a trichloromethyl and either a halo or lower alkoxy group attached to the heterocyclic ring have been known as effective fungicides. See U.S. Pat. No. 3,260,588 and No. 3,260,725, both issued to Hansjuergen A. Schroeder on July 12, 1966. However, applicants believe that until the present invention disclosed herein no one has investigated using phthalazines having these combinations of substituents as fungicides.

BRIEF SUMMARY OF THE INVENTION

The present invention is directed toward 1-halo-4-trichloromethylphthalazines and 1-lower alkoxy-4-trichloromethylphthalazines as novel compositions of matter.

The present invention also comprises a method for controlling fungi by contacting them with a fungicidally effective amount of any of these compounds or combinations thereof.

DETAILED DESCRIPTION

The above-mentioned 1-halo- or 1-lower alkoxy-4-trichloromethylphthalazine compounds may be prepared commercially from 1-halo-4-methylphthalazines by the reactions represented by equation (I) below. The starting compound is chlorinated with UV irradiation under any conventionally known conditions to convert the methyl group to a trichloromethyl group. The resulting 1-halo-4-trichloromethylphthalazine then can be converted to a 1-lower alkoxy-4-trichloromethylphthalazine compound by any conventionally known alkoxidation reaction conditions such as by employing sodium ethoxide as is illustrated in equation (I). The term "halo" as used in the present specification and claims includes chloro, bromo, and iodo groups; however, it does not include fluoro groups. The preferred halo group is chloro. The term "lower alkoxy" as used herein refers to alkoxy groups having from one to four carbon atoms. The preferred lower alkoxy group is ethoxy.

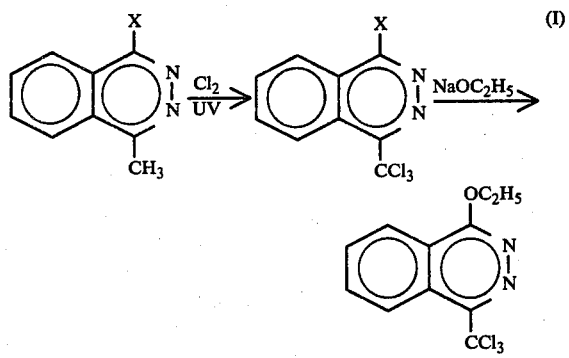

where X is a halo group.

The specific reaction conditions employed in the above-mentioned photochlorination and ethoxidation steps are not critical parameters of the present invention and any such generally known conditions for carrying out these types of such reactions may be employed herein. Thus, the present invention is not to be limited in any way to any particular method of making the above-mentioned compounds. For example, the photochlorination step can be carried out by bubbling under UV irradiation a molar excess of chlorine gas through a reactor that contains the 1-halo-4-methylphthalazine starting material in a suitable solvent such as any high boiling chlorinated benzene solvent. Preferred solvents for the photochlorination step in both of the above reaction sequences include chlorobenzene and ortho-dichlorobenzene. The reaction temperature of this photochlorination step is preferably from about 100° C. to about 160° C., more preferably from about 110° C. to about 145° C. and most preferably from about 120° C. to about 140° C. because at lower temperatures the chlorination reaction may be relatively slow. The reaction pressure is most preferably at atmospheric for economic considerations. The reaction is normally allowed to run until no change in the reaction mixture can be seen through analysis. After completion of the reaction, the 1-halo-4-trichloromethylphthalazine product can be easily recovered from the reaction mixture by any conventional recovery technique such as distillation or recrystallization.

The ethoxidation step, as indicated above in equations (I) and (II), may be carried out in any conventionally known manner. For example, it may be desirable to simply combine a suitable alkoxidation agent with 1-halo-4-trichloromethylphthalazine. Normally, alkali metal alkoxides such as sodium ethoxide are the most preferred alkoxidation agents. Sodium ethoxide is especially favored for ethoxidation reactions because it is widely commercially available today. However, it may be alternatively desirable to create the alkoxidation agent in situ in the reaction mixture. For example, this can be easily done by adding equivalent weights of sodium and a lower alcohol such as ethanol to the reaction mixture and allowing these two compounds to react to form sodium alkoxide. This just-created sodium ethoxide can then react to form the desired 1-lower alkoxy-4-trichloromethylphthalazine product. Normally, it is preferred to carry out this reaction at or below room temperature such as from about 0° C. to about 40° C. under atmospheric pressure. Furthermore, this alkoxidation reaction is usually carried out in a polar organic solvent such as tetrahydrofuran. However, it should be noted that sodium ethoxide is not stable in water. Like the photochlorination reaction, this second reaction is normally allowed to proceed until no further change in the composition of the reaction mixture was noted. Also, any conventional recovery method may be employed.

In accordance with the present invention, it has been found that 1-halo-4-trichloromethylphthalazine and 1-lower alkoxy-4-trichloromethylphthalazine, either singly or in mixtures thereof, can be utilized as fungicides. Furthermore, it has also been found that 1-lower alkoxy-4-trichloromethylphthalazine such as 1-ethoxy-4-trichloromethylphthalazine can be utilized as an effective insecticide.

In practicing the process of the present invention, fungi and insects are contacted with a fungicidally or insecticidally effective amount of these above-mentioned compounds. It is to be understood that the terms "fungicidally effective amount" and "insecticidally effective amount" as used in the specification and claims herein is intended to include any amount that will kill or control said fungi or insects when either employed by itself (i.e., in full concentration) or in sufficient concentration within a carrier or other substance. Of course, this amount may be constantly changing because of the possible variations in many parameters. Some of these may include: the number and type of fungi and insects to be controlled or killed; the type of media to which the present compounds can be applied (e.g., plants or crops, insect breeding grounds); degree of effectiveness required; and type of carrier if any.

This step of contacting may be accomplished by applying these compounds to the fungi or insects themselves, their habitat, breeding grounds, dietary media such as vegetation, crops and the like, and plant and animal life, including many which these pests may attack. In the case of fungi, it is preferable to apply the chemicals of the present invention to the dietary media or soil which they infest. In the case of insects, it may be advantageous to apply 1-lower alkoxy-4-trichloromethylphthalazines to the eggs of these insects, to the insects themselves, or to the insect larvae, the larvae habitat or the larvae dietary media. At the egg and larvae stages of the insects cycle, the insect is usually relatively stationary and the insecticide can be applied in a more economical fashion with a greater expectation of good results.

The above-mentioned compounds of the present invention may be formulated and applied by any conventional methods that include using the chemicals alone or with a carrier or other substances which may enhance the effectiveness of the chemical or facilitate handling. Moreover, the activity of the present compounds may be broadened by the addition thereto of other known biocides.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to 15% by weight of any of these four active compounds with a finely divided inert diluent such as walnut flour, diatomaceous earth, fullers earth, attaclay, talc or kaolin. Dust concentrates are made in similar fashion excepting that about 16% to 75% by weight of active compound is ground usually together with the diluent. In practice, dust concentrates are then generally admixed at the site of use with more inert diluent before it is applied to the plant foliage or animals which are to be protected from fungi or insect attack.

Wettable powders are generally prepared in the same manner as dust concentrates, but usually about 1% to 10% by weight of a dispersing agent, for example, an alkali metal lignosulfonate and about 1% to 10% of a surfactant, such as a non-ionic surfactant, are incorporated in the formulation. For application to agronomic crops, shrubs, ornamentals and the like, the wettable powder is usually dispersed in water and applied as a spray. For treatment of warm-blooded animals, this same spray-type application may be used or the wettable powder may be dispersed in the water of a dipping trough through which the animals are driven.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds, or more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that the fungicide or insecticide formulations, the ingredients which may make up such formulations other than the active compounds and the dosages, and means of applying these formulations may include all known and conventional substances, amounts and means, respectively, that are suitable for obtaining the desired fungicidal and/or insecticidal result. And, therefore, such process parameters are not critical to the present invention.

Fungicides and insecticides of the present invention may be effective for the control of broad classes of fungi and insects and the latter's eggs and larvae. Specific illustrations of fungi wherein fungicidal activity has been shown include bean powdery mildew, rice leaf spot and bean rust. Specific illustrations of insects wherein insecticidal activity has been shown include Southern armyworm larvae and Mexican bean beetle larvae.

The following examples further illustrate the present invention. All parts and percentages employed therein are by weight unless otherwise indicated.

EXAMPLE I

Preparation of 1-chloro-4-trichloromethylphthalazine

50 Grams (0.28 gram-moles) of 1-chloro-4-methylphthalazine was placed in 500 milliliters of chlorobenzene in a glass reaction vessel. Gaseous chlorine was bubbled up through the reaction mixture while the reaction temperature was held at reflux temperature (approximately 130° C.). During this time the reaction mixture was exposed to UV irradiation from a high intensity UV lamp. The chlorination was monitored by Vapor Phase Chromatography (VPC) and was continued until no further change in the composition of the reaction mixture was noted. Most of the solvent was then removed by vacuum distillation and a solid residue remained which was dried. The dried product weighed 49.1 grams and had a melting point of about 146°–149° C. Elemental and mass spectral analyses confirm the product as 1-chloro-4-trichloromethylphthalazine.

EXAMPLE II

Preparation of 1-ethoxy-4-trichloromethylphthalazine

14 Grams (0.05 gram-moles) of 1-chloro-4-trichloromethylphthalazine was placed in 150 ml of ethanol in a glass reaction vessel. A solution of 1.2 grams (0.05 mole) of sodium in ethanol was added and the mixture refluxed at room temperature for 2 hours. The sodium and ethanol reacted to form sodium ethoxide in situ which in turn reacted with the phthalazine compound. The solids present in the reaction mixture were first filtered off leaving a liquid filtrate. This filtrate was then cooled to crystallize a solid product. The filtrate was removed and the product dried. The product weighed 6.1 grams of product with a melting point of 171°–172° C. Elemental and mass spectral analyses confirmed that the product was 1-ethoxy-4-trichloromethylphthalazine.

These active materials formed in Examples 1 and 2 were then tested for activity as effective foliar fungicides and in the case of the latter compound, as an effective insecticide.

A uniform aqueous dispersion of each chemical was first prepared. This dispersion was made by dissolving each chemical in a solution of acetone containing the surfactant TRITON X-155[1] (concentration 1000 parts per million). Next, this solution is diluted with water 1:9 to obtain a stock solution of 10% by volume acetone and 90% by volume water with 100 ppm TRITON X-155 and the test chemical contained therein. This stock solution was diluted further with water/acetone mix to provide the desired concentration of the test material, if required.

[1] Manufactured by Rohm and Haas of Philadelphia, Pa. and is a polyether alcohol.

The aqueous solutions containing each chemical were applied to various plants according to the methods stated below. These tests were designed to evaluate the ability of each chemical to protect non-infected foliage and eradicate recently established infection against major types of fungi such as leaf spot, rust, and mildew that attack above-ground parts of plants.

EXAMPLES III AND IV

Bean plants with incipient infection of bean powdery mildew, (*Erysiphe polygoni* DC) which have fully expanded leaves and are in 2½ inch pots are atomized (sprayed) with an aqueous solution of one of the chemicals of the present invention. The aqueous solution contained 260 parts per million of each chemical and the atomization operation occurred while rotating the plants on a turntable. Immediately afterwards, the potting soil was drenched with 21 ml of a 520 ppm stock solution (equivalent to 25 lb/acre) for each chemical. After seven days, observations are made on the eradication of established infection present on the primary leaves at the time of spraying. The leaves are rated on a scale of from 0 (no suppression) to 10 (complete eradication or prevention of infection). The test results are given in Table 1 below.

EXAMPLE V

Pinto beans, which were in 2½ inch pots and 9 to 12 days old, were sprayed with an aqueous solution of 1-chloro-4-trichloromethylphthalazine. The young plants were sprayed while rotating the plants on a turntable and the aqueous solution contained 260 parts per million of the chemical. At the same time, 21 milliliters of an aqueous solution containing 520 parts per million was poured on the surface of the potting soil. After the spray deposit had dried, the plants were atomized with a suspension of uredospores [summer spore stages of Bean rust (*Uromyces phaseoli*)] and placed in a moist chamber at 70° F. for 24 hours. After 7 to 9 days the severity of pastule formation is rated on a scale of from 0 (no inhibition) to 10 (complete inhibition). The test results are given in Table I below.

EXAMPLES VI AND VII

The fully expanded young leaves of a rice, cultivar Starr Bonnet, which were about two weeks old and growing in 2½ inch pots, were sprayed with an aqueous solution which contained a chemical of the present invention. The young plants were sprayed while rotating on a turntable with the aqueous solution which contained 260 ppm of the chemical. Immediately afterwards, the soil in each pot was drenched with 21 milliliters of a 520 ppm suspension (equivalent to 25 lb/acre) of the chemical. After the spray dries, the plants were atomized with a conidial suspension of Rice brown spot (*Helminthospoium oryzae* B. de H.) and placed in a moist chamber at 75° F. for 24 hours to facilitate infection. After discrete lesions appear in the unprotected controls (two days later), the infection is rated on a scale of from 0 (no inhibition) to 10 (complete inhibition of infection). The test results are given in Table I below.

TABLE I

| | | FUNGICIDAL ACTIVITY | | | |
| | | Conc. of Chemical | Effectiveness Against | | |
| Example | Chemical | in Solution | Powdery Mildew | Bean Rust | Rice Leaf Spot |
| III | 1-chloro-4-trichloromethylphthalazine | 260 ppm | 8.0 | | |
| IV | 1-ethoxy-4-trichloromethylphthalazine | 260 ppm | 7.0 | | |
| V | 1-chloro-4-trichloromethylphthalazine | 260 ppm | | 10.0 | |
| VI | 1-chloro-4-trichloromethylphthalazine | 260 ppm | | | 6.0 |
| VII | 1-ethoxy-4-trichloromethylphthalazine | 260 ppm | | | 6.0 |

EXAMPLES VIII AND IX

Leaves of young bean plants were dipped in an aqueous solution containing 260 ppm (or 33 parts per million) of 1-ethoxy-4-trichloromethylphthalazine. Next, 5- to 7-day old larvae of Southern armyworm, [*Prodenia eridania* (Cramer)], are placed upon them as soon as the chemical is dry. Observations are made on the extent of inhibition of feeding two or three days later. This response was rated from 0 (no effect on feeding) to 10 (total inhibition of feeding). The results are given in Table II below.

EXAMPLE X

Leaves of young bean plants were dipped in an aqueous solution containing 260 parts per million of 1-ethoxy-4-trichloromethylphthalazine. Next, 5- to 7-day old larvae of Mexican bean beetle, (*Epilachna varivestis* Mulsart), are placed upon them as soon as the chemical is dry. Observations are made on the extent of inhibition of feeding two or three days later. This response was rated from 0 (no effect on feeding) to 10 (total inhibition of feeding). The results are given in Table II below.

Table II

| | | INSECTICIDAL ACTIVITY | | |
| | | | Control of Feeding | |
| Example | Chemical | Conc. of Chemical in Solution | Southern Armyworm | Mexican Bean Beetle |
| --- | --- | --- | --- | --- |
| VIII | 1-ethoxy-4-trichloromethylphthalazine | 260 ppm | 10.0 | |
| IX | 1-ethoxy-4-trichloromethylphthalazine | 33 ppm | 6.0 | |
| X | 1-ethoxy-4-trichloromethylphthalazine | 260 ppm | | 3.0 |

What is claimed is:

1. A method of controlling fungi which comprises contacting said fungi with a fungicidally effective amount of a compound having the formula

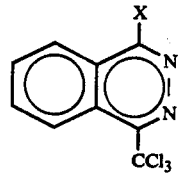

where X is either a halo group or a lower alkoxy group.

2. The method of claim 1 wherein said compound is 1-halo-4-trichloromethylphthalazine.

3. The method of claim 1 wherein said compound is 1-chloro-4-trichloromethylphthalazine.

4. The method of claim 1 wherein said compound is 1-lower alkoxy-4-trichloromethylphthalazine.

5. The method of claim 1 wherein said compound is 1-ethoxy-4-trichloromethylphthalazine.